US007008905B2

(12) United States Patent

Baltruschat et al.

(10) Patent No.: US 7,008,905 B2
(45) Date of Patent: Mar. 7, 2006

(54) METHOD OF COMBATING UNDESIRED PLANT GROWTH ON CEREALS

(75) Inventors: Helmut Siegfried Baltruschat, Schweppenhausen (DE); Axel Kleemann, Königstein (DE); Thomas Maier, Stockach (DE); Stefan Scheiblich, Mainz (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1123 days.

(21) Appl. No.: 09/861,006

(22) Filed: May 18, 2001

(65) Prior Publication Data

US 2002/0049141 A1 Apr. 25, 2002

Related U.S. Application Data

(60) Provisional application No. 60/205,952, filed on May 19, 2000.

(51) Int. Cl.
*C07D 239/34* (2006.01)
*A01N 43/54* (2006.01)

(52) U.S. Cl. ....................................... 504/242; 544/319

(58) Field of Classification Search ................ 544/319; 504/242

See application file for complete search history.

(56) References Cited

U.S. PATENT DOCUMENTS

| | | | | |
|---|---|---|---|---|
| 5,824,624 | A | 10/1998 | Kleeman et al. | 504/242 |
| 5,849,758 | A | 12/1998 | Kleemann et al. | 514/269 |
| 6,281,358 | B1 * | 8/2001 | Meyer et al. | 544/319 |

* cited by examiner

*Primary Examiner*—Deepak Rao
(74) *Attorney, Agent, or Firm*—Novak Druce & Quigg LLP

(57) ABSTRACT

A method of combating undesired plant growth in cereals, in particular winter cereals such as wheat and barley, which comprises treating the locus of the cereals with an effective amount of one or more compounds of formula I:

(I)

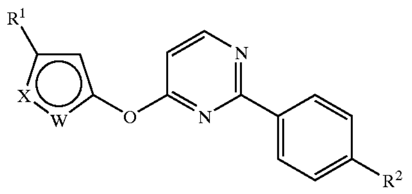

in which $R^1$, $R^2$ and X—W have the meaning given in the claims.

23 Claims, No Drawings

METHOD OF COMBATING UNDESIRED PLANT GROWTH ON CEREALS

This application claims priority from copending provisional application Ser. No. 60/205,952 filed on May 19, 2000.

BACKGROUND OF THE INVENTION

This invention relates to a method of combating undesired plant growth on cereals using an effective amount of certain 4-aryloxy-2-phenylpyrimidine compounds.

Pyrimidines and their derivatives have many uses in the pharmaceutical area as well as in agriculture (e.g., herbicides, fungicides, acaricides, anthelmintics, bird repellents), and as reagents, intermediates and chemicals for the polymer and textile industry.

The U.S. Pat. Nos. 5,824,624 and 5,849,758 disclose herbicidal 2-aryloxy-6-phenylpyridines and 4-aryloxy-2-phenylpyrimidines. However, these patents disclose only 4-aryloxy-2-phenylpyrimidines in which the central pyrimidine group exhibits an additional substituent in the 5- and/or 6-position.

Although some known compounds show considerable activity against various weeds, they are not completely satisfying with regard to their selectivity in cereals such as winter wheat or winter barley. Therefor it was an object of the present invention to provide a novel method to combat undesired plant growth in cereals. Furthermore it is an object of the present invention to provide novel compounds with improved herbicidal properties.

The present invention provides a method of combating undesired plant growth in cereals, which comprises treating a locus associated with the cereals with an effective amount of one or more compounds of formula I:

(I)

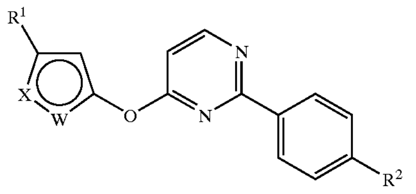

in which

X—W represents N—N($CH_3$), N—CH—CH or CH—CH—CH;

$R^1$ represents a halogen atom or a haloalkyl or haloalkoxy; and $R^2$ represents a halogen atom or a haloalkyl group.

The compounds of formula I have excellent herbicidal activity against weeds and relatively low phytotoxicity in winter cereals, such as winter wheat and winter barley, and degrade well in soil.

The method according to the present invention provides a combination of high herbicidal activity against a broad range of undesired grasses and broadleaf weeds with high selectivity in cereals and a desirable rate of degradation in soil.

Furthermore the invention provides compounds of formula I and herbicidal compositions comprising the compounds I and having a very good herbicidal activity.

These and other objects and features of the invention will become more apparent from the detailed description set forth below.

It has surprisingly been found that the compounds of formula I, in which $R^1$, $R^2$ and X—W have the meaning given above, show excellent herbicidal activity against a broad range of weeds without damaging the cereals.

The alkyl portion of a haloalkyl or haloalkoxy group suitably has from 1 to 4 carbon atoms, preferably 1 or 2 carbon atoms. Haloalkyl moieties of any groups within the definitions used herein may contain one or more halogen atoms. Haloalkyl and haloalkoxy groups are preferably mono-, di-, tri- or perfluoroalkyl and -alkoxy groups, especially trifluoromethyl, pentafluoroethyl, trifluoromethoxy, difluoromethoxy or 2,2,2-trifluoroethoxy groups.

In the invention described herein, the term "halogen" means a fluorine, chlorine, bromine or iodine atom, preferably fluorine or chlorine.

Compounds suitable for use in this invention include compounds of formula I, as well as isotopes thereof, geometric and stereoisomers thereof, N-oxides thereof, and agriculturally suitable salts thereof. These compounds can exist as one or more stereoisomers. Suitable isotopes include compounds of formula I in which at least one natural occurring isotope such as a hydrogen or $^{12}C$ carbon atom is replaced by another isotope thereof such as deuterium or $^{13}C$. Suitable stereoisomers may include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Techniques for separating, enriching, and/or selectively preparing said stereoisomers are well-known in the art. The compounds of formula I may be present as a mixture of stereoisomers, individual stereoisomers, or in an optically active form.

One skilled in the art will appreciate that not all nitrogen containing heterocycles can form N-oxides, and will recognize those which can form N-oxides. Synthetic methods for the preparation of N-oxides of heterocycles are well known in the art; these include the oxidation of heterocycles with peroxy compounds, such as peracetic acid and m-chloroperbenzoic acid (MCPBA), hydrogen peroxide, and alkylhydroperoxides such as tert-butyl hydroperoxide. Such methods for the preparation of N-oxides have been described and reviewed in the literature, for example: T. L. Gilchrist in *Comprehensive Organic Synthesis*, vol. 7, pp 748–750 and in *Advances in Heterocyclic Chemistry*, vol. 9, pp 285–291, vol. 22, pp 390–392 and vol. 43, pp 149–161, A. R. Katritzky. Ed., Academic Press.

The salts of the compounds of the invention include acid-addition salts of inorganic and organic acids such as hydrobromic, hydrochloric, nitric, phosphoric, sulfuric, acetic, butyric, fumaric, lactic, maleic, oxalic, propionic salicylic, tartaric, toluenesulfonic or valeric acids.

Preferred compounds of formula I, in the practice of this invention, include those wherein

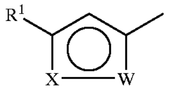

represents a group selected from the formulae a and b:

(a)

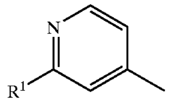

(b)

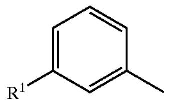

in which $R^1$ is a halogen atom or a $C_{1-4}$ fluoroalkyl group, most preferably a chlorine atom, or a trifluoromethyl group.

Particularly preferred are the compounds of formula IA:

(IA)

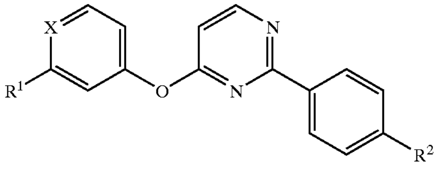

wherein $R^1$ and $R^2$ represent a haloalkyl group; and X represents CH or N.

Especially preferred compounds of this invention include: 4-(3-trifluoromethylphenoxy)-2-(4-trifluoromethyl-phenyl)-pyrimidine ("TTP") and 4-(2-chloropyrid-4-yloxy)-2-(4-trifluoromethyl-phenyl)pyrimidine ("CTP").

The compounds of formula I may be oils, gums, or crystalline solid materials. They can be used in agriculture or related fields for the control of undesired plants, especially for the selective control of undesired plants such as *Alopecurus myosuroides, Apera spica-venti, Poa annua, Galium aparine, Matricaria inodora* and *Stellaria media* by pre- and postemergence application, in certain winter cereals, such as barley and wheat.

The compounds of formula I can be prepared analogously to the methods disclosed in U.S. Pat. No. 5,824,624.

A suitable process for the preparation of the compounds of formula I comprises the reaction of a compound of formula II (II)

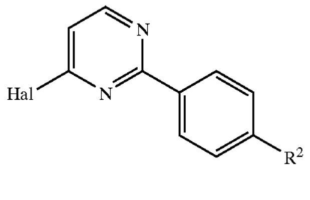

with a compound of formula III (III)

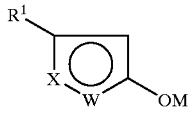

wherein $R^1$, $R^2$, X and W are as defined hereinbefore; Hal represents a halogen atom; and M represents a metal atom.

The halogen atom Hal may be any halogen atom, suitable a fluorine, chlorine or bromine atom. The metal atom M may be any metal atom, suitable alkali metal atoms. Sodium and potassium being preferred.

The reaction of compounds of formulae II and III may be carried out in analogy to usual conditions know by a person skilled in the art or for example as mentioned in U.S. Pat. No. 5,824,624.

A process for the preparation of compounds of formula II comprises the reaction of benzamidine hydrochlorides of formula IV (IV)

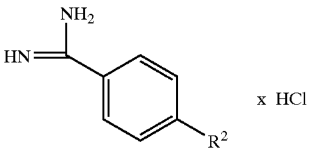

wherein $R^2$ is as defined hereinbefore with a compound of formula V or derivatives thereof (V)

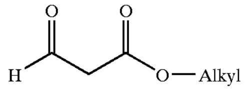

to give a pyrimidinone of formula VI.

(VI)

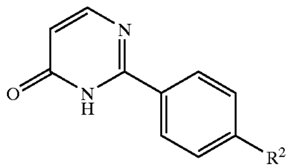

The reaction of compounds of formulae IV and V may be carried out according to Liebigs Ann. 1980, 1393 f in an organic solvent, suitable an alcohol and preferably ethanol and in the presence of a base, suitable metal alkoxides, preferably sodium ethoxides.

Compounds of formula VI may subsequently be converted into compounds of formula II essentially as described in Davies and Pigott, J. Chem. Soc. 1945, 347 by reaction with a phosphoryl halogenide or thionyl halogenide or phosgene, preferably phosphoryl chloride, phosphoryl bromide, ideally in the absence of a solvent, at elevated temperatures to obtain compounds of formula II.

Compounds of formula III are know or may be prepared by known methods. They may be prepared and isolated separately or may be prepared in situ. Generally a compound of formula VII (VII)

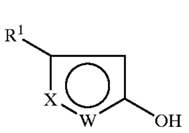

wherein, X, W and $R^1$ are as hereinbefore defined is reacted with a Suitable metal base, for example a metal carbonate or hydride. Preferably the metal salt is a sodium or potassium salt.

The method of combating undesired plant growth according to the present invention is conventionally carried out by foliar spray application; the locus is most suitably plants in a cereal field. However, application may also be to the soil, in the case of pre-emergence applications. The dosage or application rate of the active ingredient to the locus may, e.g., be in the range of from 0.005 to 0.5 kg/ha, especially 0.01 to 0.5 kg/ha, preferably 0.02 to 0.3 kg/ha.

However the preferred dose rates may differ depending an the weed and other factors. The following dose rates are particularly preferred for the indicated weeds:

Alopecurus and Poa:
from 0.15 to 0.28, preferably from 0.20 to 0.25 kg/ha;

Apera:
from 0.03 to 0.15, preferably 0.05 to 0.10 kg/ha;

Galium, Matricaria and Stellaria:
from 0.05 to 0.15, preferably 0.10 to 0.13 kg/ha.

The compounds of formula I as defined above suitably are applied in association with at least one carrier. Preferably, there are at least two carriers, at least one of which is a surface-active agent.

The invention also provides a method of combating undesired plant growth an cereals, comprising application of such a compound or a composition thereof. Such a composition may contain a single active ingredient or a mixture of several active ingredients of the present invention. Different isomers or mixtures of isomers may have different levels or spectra of activity, and compositions of this invention may comprise individual isomers or mixtures of isomers.

A composition according to the invention preferably contains from 0.5% to 95% by weight (w/w) of active ingredient.

A carrier in a composition according to the invention may be any material with which the active ingredient is formulated to facilitate application to the locus to be treated (which locus may be, e.g., a plant, seed or soil), or to facilitate storage, transport or handling. A carrier may be a solid or a liquid, including material which is normally a gas but which has been compressed to form a liquid.

The compositions may be manufactured in various forms, e.g. emulsion concentrates, solutions, oil in water emulsions, wettable powders, soluble powders, suspension concentrates, dusts, granules, water dispersible granules, microcapsules, aerosols and gels, by well-established procedures. These procedures may include intensive mixing and/or milling of the active ingredients with other substances, such as fillers, solvents, solid carriers, surface active compounds (surfactants), and/or solid or liquid auxilaries or adjuvants. The form of the composition and the application method (such as spraying, atomizing, dispersing or pouring) may be readily selected by those skilled in the art based on the desired objectives and the given circumstances.

Solvents (liquid carrier) useful in this invention may be aromatic hydrocarbons, e.g. Solvesso® 200, substituted naphthalenes, phthalic acid esters (such as dibutyl or dioctyl phthalate), aliphatic hydrocarbons (e.g. cyclohexane or paraffins), alcohols and glycols (as well as their ethers and esters, e.g. ethanol, ethyleneglycol mono- and dimethyl ether), ketones (such as cyclohexanone), strongly polar solvents (such as N-methyl-2-pyrrolidone, or g-butyrolactone), higher alkyl pyrrolidones (e.g. n-octylpyrrolidone or cyclohexylpyrrolidone), epoxidized plant oil esters (e.g. methylated coconut or soybean oil ester) and water. Mixtures of solvents are often suitable in the practice of this invention.

Solid carriers, which may be used for making formulations of the invention in the form of dusts, wettable powders, water dispersible granules, or granules, may include mineral fillers, such as calcite, talc, kaolin, montmorillonite or attapulgite. The physical properties of such formulations may be modified or improved by addition of highly dispersed silica gel or polymers, if desired. Carriers for granules according to the invention may be porous material, e.g. pumice, kaolin, sepiolite, bentonite; or non-sorptive material, e.g., calcite or sand. Additionally, a multitude of pregranulated inorganic or organic materials may be used, such as dolomite or crushed plant residues.

Pesticidal compositions of this invention may be formulated and transported in a concentrated form which is subsequently diluted by the user before application. The presence of small amounts of a carrier which is a surfactant facilitates this process of dilution. Thus, preferably at least one carrier in a composition according to the invention is a surfactant.

Suitable surfactants (surface active agent) for this invention include nonionic, anionic, cationic and zwitterionic substances having good dispersing, emulsifying and wetting properties. The suitability of a surfactant for a particular formulation may be readily determined by those skilled in the art based an the nature of the compound of formula I to be formulated. Mixtures of individual surfactants may also be used.

Wettable powders of the present invention suitably contain 5 to 90% w/w of active ingredient, a solid inert carrier, 3 to 10% w/w of dispersing and wetting agents, and 0 to 10% w/w of stabilizer(s) and/or other additives such as penetrants or stickers. Dusts are suitably are formulated as a dust concentrate having a similar composition to that of a wettable powder but without a dispersant, and may be diluted in the field with further solid carrier to give a composition containing, e.g., about 0.5 to 10% w/w of active ingredient. Water dispersible granules and other granules of this invention suitably are between 0.15 mm and 2.0 mm in diameter and may be manufactured by a variety of techniques known in the art. Generally, the granules contain about 0.5 to 90% w/w active ingredient and about 0 to 20% w/w of additives such as stabilizer, surfactants, slow release modifiers and binding agents.

Emulsifiable concentrates of this invention may contain a solvent or a mixture of solvents, about 1 to 80% w/v active ingredient, about 2 to 20% w/v emulsifiers and about 0 to 20% w/v of other additives such as stabilizers, penetrants and corrosion inhibitors. Suspension concentrates may be milled to obtain a stable, non-sedimenting, flowable product containing about 5 to 75% w/v active ingredient, about 0.5 to 15% w/v of dispersing agents, about 0.1 to 10% w/v of suspending agents such as protective colloids and thixotropic agents, about 0 to 10% w/v of other additives such as defoamers, corrosion inhibitors, stabilizers, penetrants and stickers, and either water or an organic liquid in which the active ingredient is substantially insoluble; organic solids or inorganic salts may be present dissolved in the formulation to assist in preventing sedimentation and crystallization, or as antifreeze agents for water.

Aqueous dispersions and emulsions, including compositions obtained by diluting the formulated product according to the Invention with water, also lie within the scope of the invention.

If desired, the duration of the protective activity of the compounds of this invention may be extended by the use of a carrier which will provide slow release of the pesticidal compounds, e.g., as disclosed by U.S. Pat. No. 5,705,174, the full disclosure of which is incorporated herein by reference.

The biological activity of the active ingredient may be increased by including an adjuvant in the composition. An adjuvant is defined here as a substance which can increase the biological activity of an active ingredient but is not itself significantly biologically active. The adjuvant can either be included in the formulation, or can be mixed with it prior to application, e.g., added to the spray tank together with the formulation containing the active ingredient.

As a commodity, the compositions may be in a concentrated form which the end user will dilute to a concentration as low as about 0.001% of active ingredient. Preferred application rates are in the approximate range of from 0.01 to 10 kg a.i./ha.

Examples of formulations in accordance with the invention are:

| Emulsion Concentrate (EC) | | |
|---|---|---|
| Active Ingredient | TTP | 30% (w/v) |
| Emulsifier(s) | Atlox ® 4856 B/Atlox ® 4858 B[1)] (mixture containing calcium alkyl aryl light sulfonate, fatty alcohol ethoxylates and aromatics/mixture containing calcium alkyl and aryl sulfonate, fatty alcohol ethoxylates and lightaromatics) | 5% (w/v) |
| Solvent | Shellsol ® A[2)] (mixture of $C_9$–$C_{10}$ aromatic hydrocarbons) | to 1000 ml |

| Suspension Concentrate (SC) | | |
|---|---|---|
| Active Ingredient | TTP | 50% (w/v) |
| Dispersing agent | Soprophor ® FL[3)] (polyoxyethylene polyaryl phenyl ether phosphate amine salt) | 3% (w/v) |
| Antifoaming agent | Rhodorsil ® 422[3)] (nonionic aqueous emulsion of polydimethylsiloxanes) | 0.2% (w/v) |
| Structure agent | Kelzan ® S[4)] (Xanthan gum) | 0.2% (w/v) |
| Antifreezing agent | Propylene glycol | 5% (w/v) |
| Biocidal agent | Proxel ®[5)] (aqueous dipropylene glycol solution containing 20% 1,2-benisothiazolin-3-one) | 0.1% (w/v) |
| Water | | to 1000 ml |

| Wettable Powder (WP) | | |
|---|---|---|
| Active Ingredient | TTP | 60% (w/w) |
| Wetting agent | Atlox ® 4995[1)] (polyoxyethylene alkyl ether) | 2% (w/w) |
| Dispersing agent | Witcosperse ® D-60[6)] (mixture of sodium salts of condensed naphthalene sulfonic acid and alkylarylpolyoxy acetates | 3% (w/w) |
| Carrier/Filler | Kaolin | 35% (w/w) |

| Water Dispersible Granules (WG) | | |
|---|---|---|
| Active Ingredient | TTP | 50% (w/w) |
| Dispersing/Binding agent | Witcosperse ® D-450[6)] (mixture of sodium salts of condensed naphthalene sulfonic acid and alkyl sulfonates) | 8% (w/w) |
| Wetting agent | Morwet ® EFW[6)] (formaldehyde condensation product) | 2% (w/w) |
| Antifoaming agent | Rhodorsil ® EP 6703[3)] (encapsulated silicone) | 1% (w/w) |
| Disintegrant | Agrimer ® ATF[7)] (cross-linked homopolymer of N-vinyl-2-pyrrolidone) | 2% (w/w) |
| Carrier/Filler | Kaolin | 35% (w/w) |

[1)]available from ICI Surfactants
[2)]available from Deutsche Shell AG
[3)]available from Rhône-Poulenc
[4)]available from Kelco Co.
[5)]available from Zeneca
[6)]available from Witco
[7)]available from International Speciality Products The compositions of this invention can be applied to the plants or their environment simultaneously with or in succession with other active substances. These other active substances can be either fertilizers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

The active ingredients according to the invention can be employed alone or as formulations in combination with conventional herbicides. Such combinations of at least two herbicides can be included in the formulation or added in a suitable form when a tank mix is prepared. For such mixtures, the conventional herbicides may be selected from: ametrydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, oxasulfuron, azimsulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop-M-isopropyl, picolinafen, fluthiamid, isoxaflutole, flurtamone, daimuron, bromobutide, methyldimron, dimethenamid, sulcotrione, sulfentrazone, oxadiargyl, acifluorfen, cafenstrole, carfentrazone, diuron, and glufosinate.

Mixtures of compositions or compounds of the present invention with other active ingredients like fungicides, insecticides, acaricides and nematicides are possible.

An example of a suitable concentrated formulation of the present invention is one consisting essentially of 100 g of one or more active ingredients (including at least one compound of formula I), 30 g of dispersing agents, 3 g of one or more antifoaming agents, 2 g of one or more structure agents, 50 g of one or more anti-freezing agents, 0.5 g of a biocidal agent and water ad 1000 ml. Prior to use, this concentrated formulation may be diluted with water to achieve the desired concentration of active ingredient(s).

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the invention.

Herbicidal Activity

To evaluate their herbicidal activity, compounds according to the invention are tested using a representative range of plants:

| | |
|---|---|
| TRZAWK | *Triticum aestivum* variety "Kanzler" |
| TRZAWM | *Triticum aestivum* variety "Monopol" |
| HORVWM | *Hordeum vulgare* variety "Mammut" |
| HORVWN | *Hordeum vulgare* variety "Catania" |
| ALOMY | *Alopecurus myosuroides* |
| APESV | *Apera spica-venti* |
| POAAN | *Poa annua* |
| SETVI | *Setaria viridis* |
| LOLPE | *Lolium perenne* |
| GALAP | *Galium aparine* |
| LAMPU | *Lamium purpureum* |
| MATIN | *Matricaria inodora* |
| POLCO | *Polygonum convolvulus* |

-continued

| | |
|---|---|
| STEME | *Stellaria media* |
| VERPE | *Veronica persica* |

The following compounds have been tested:

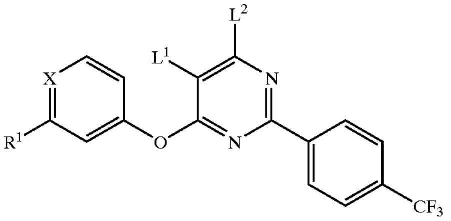

| Compound | X | $R^1$ | $L^1$ | $L^2$ | Origin |
|---|---|---|---|---|---|
| TTP | CH | $CF_3$ | H | H | Invention |
| REF-1 | CH | $CF_3$ | $CH_3$ | H | U.S. Pat. No. 5,849,758, example 115 |
| REF-2 | CH | $CF_3$ | $CH_3$ | $CH_3$ | U.S. Pat. No. 5,849,7580, example 130 |
| REF-3 | CH | $CF_3$ | H | $C_2H_5$ | U.S. Pat. No. 5,849,758, example 138 |
| CTP | N | Cl | H | H | Invention |
| REF-4 | N | Cl | $CH_3$ | H | U.S. Pat. No. 5,849,758, example 128 |
| REF-5 | N | Cl | $CH_3$ | $CH_3$ | U.S. Pat. No. 5,849,758 |
| REF-6 | N | Cl | H | $CH_3$ | U.S. Pat. No. 5,849,758 |
| REF-7 | N | Cl | H | $SCH_3$ | U.S. Pat. No. 5,849,758, example 193 |
| REF-8 | N | Cl | $OCH_3$ | H | U.S. Pat. No. 5,849,758, example 179 |

1. Pre-Emergence Test

The pre-emergence tests involve spraying a liquid formulation of the compound onto the soil in which the seeds of the plant species mentioned above has recently been sown.

The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155.

These acetone solutions are diluted with water and the resulting formulations applied at dosage levels corresponding to 15 g, 30 g, 60 g, 120 g or 240 g of active material per hectare in a volume equivalent to 900 liters per hectare. In these tests untreated sown soil is used as control. The herbicidal effects of the test compounds are assessed visually three weeks after spraying the soil and are recorded an a 0 to 100 scale. A rating 0 indicates growth as untreated control, a rating 100 indicates death. An increase of 10 unit an the linear scale approximates to a 10% increase in the level of effect. The results of the assessment are set out in Tables 1 to 4.

TABLE 1

| Treatment | Dose kg/ha | Pre-emergence application 3 weeks after treatment (Weed control) ALOMY | APESV | POAAN | SETVI | LOLPE | GALAP | LAMPU | MATIN | POLCO | STEME | VERPE |
|---|---|---|---|---|---|---|---|---|---|---|---|---|
| TTP | 0.240 | 100 | 100 | 100 | 100 | 100 | 93 | 100 | 100 | 100 | 100 | 100 |
| | 0.120 | 100 | 100 | 100 | 100 | 99 | 75 | 100 | 100 | 100 | 100 | 100 |
| | 0.060 | 90 | 100 | 100 | 100 | 99 | 50 | 100 | 100 | 100 | 100 | 100 |
| | 0.030 | 50 | 100 | 100 | 100 | 99 | 30 | 100 | 99 | 100 | 99 | 100 |
| | 0.015 | 15 | 100 | 100 | 100 | 70 | 5 | 99 | 98 | 80 | 99 | 100 |
| REF-1 | 0.240 | 100 | 100 | 100 | 100 | 100 | 95 | 100 | 100 | 100 | 100 | 100 |
| | 0.1 | 100 | 100 | 100 | 100 | 100 | 75 | 100 | 100 | 100 | 100 | 100 |
| | 0.060 | 100 | 100 | 100 | 100 | 99 | 50 | 100 | 100 | 100 | 100 | 100 |
| | 0.030 | 92 | 100 | 100 | 100 | 95 | 15 | 100 | 99 | 93 | 90 | 100 |
| | 0.015 | 65 | 100 | 98 | 93 | 80 | 5 | 100 | 99 | 92 | — | 100 |
| REF-2 | 0.240 | 70 | 100 | 100 | 100 | 97 | 50 | 100 | 99 | 80 | 100 | 100 |
| | 0.120 | 65 | 100 | 100 | 100 | 93 | 5 | 98 | 99 | 30 | 97 | 100 |
| | 0.060 | 15 | 98 | 97 | 97 | 60 | 3 | 75 | 98 | 0 | 20 | 100 |
| | 0.030 | 5 | 85 | 95 | — | 30 | 0 | 40 | 98 | 0 | — | 99 |
| | 0.015 | 0 | 80 | 65 | 65 | 5 | 0 | — | 95 | 0 | 0 | 25 |
| REF-3 | 0.240 | 100 | 100 | 100 | 100 | 100 | 97 | 100 | 100 | 100 | 100 | 100 |
| | 0.120 | 100 | 100 | 100 | 100 | 99 | 85 | 100 | 100 | 100 | 100 | 100 |
| | 0.060 | 98 | 100 | 100 | 100 | 99 | 50 | 100 | 99 | 80 | 100 | 100 |
| | 0.030 | 98 | 100 | 100 | 100 | 98 | — | 100 | 99 | 70 | 100 | 100 |
| | 0.015 | 55 | 100 | 100 | 100 | 90 | — | 100 | 99 | 25 | 98 | 100 |

TABLE 2

| Treatment | Dose kg/ha | Pre-emergence application 3 weeks after treatment (Selectivity) HORVWM | HORVW | TRZAWK | TRZAWM |
|---|---|---|---|---|---|
| TTP | 0.240 | 45 | 55 | 10 | 15 |
| | 0.120 | 40 | 50 | 3 | 5 |
| | 0.060 | 30 | 30 | 0 | 1 |
| | 0.030 | 22 | 25 | 0 | 0 |
| | 0.015 | 5 | 10 | 0 | 0 |
| REF-1 | 0.240 | 65 | 65 | 40 | 45 |
| | 0.120 | 60 | 60 | 25 | 30 |
| | 0.060 | 45 | 55 | 25 | 25 |
| | 0.030 | 45 | 45 | 10 | 12 |
| | 0.015 | 25 | 35 | 3 | 3 |
| REF-2 | 0.240 | 25 | 30 | 5 | 5 |
| | 0.120 | 18 | 20 | 1 | 2 |
| | 0.060 | 5 | 10 | 1 | 1 |
| | 0.030 | 3 | 10 | 1 | 1 |
| | 0.010 | 0 | 0 | 0 | 0 |
| REF-3 | 0.240 | 55 | 60 | 40 | 45 |
| | 0.120 | 55 | 60 | 25 | 35 |
| | 0.060 | 40 | 45 | 8 | 10 |
| | 0.030 | 30 | 45 | 8 | 8 |
| | 0.015 | 20 | 15 | 5 | 3 |

Wheat

TTP was sufficiently selective in wheat at the highest dose of 240 g/ha. Furthermore, TTP controlled at wheat selective doses all of the grass and broadleaf weeds including the grass Alopecurus and the broadleaf weed Galium, both of which are considered to be the most important weeds in European cereals.

All the compounds of the prior art except REF-2 were less selective in wheat than TTP.

The maximum tolerated dose in wheat was 120 g/ha for REF-1. Furthermore, all the compounds except REF-1 were considerably less active than the compound of the invention an key weeds.

The compounds of the prior art, REF-1 and REF-3, were the most aggressive compounds in wheat. REF-3 was tolerated in wheat at 60 g/ha and REF-1 at 30 g/ha, respectively. At wheat selective doses none of the compounds of the prior art controlled the key broadleaf weed *Galium aparine.*

Barley

TTP was sufficiently selective in barley at 15 g/ha effectively controlling at this dose still a broad spectrum of grasses and broadleaf weeds such as Apera, Poa, Setaria, Lamium, Matricaria, Stellaria and Viola. The most active compounds of the prior art, REF-1, did not exhibit acceptable tolerance in barley at any dose.

Conclusions

TTP was the only compound that provided complete pre-emergencecontrol of all the grasses and broadleaf weeds including Alopecurus, Galium and Lolium at wheat selective doses, thus, clearly demonstrating the considerably high potential, this compound offers for pre-emergence weed control in wheat. Contrary to the compounds of the prior art, TTP in addition shows good opportunities for barley selective control of a broad spectrum of grasses and broadleaf weeds such as Apera, Poa, Setaria, Lamium, Matricaria, Stellaria and Veronica.

TABLE 3

Pre-emergence application 3 weeks after treatment (Weed control)

| Treatment | Dose kg/ha | ALOMY | APESV | POAAN | SETVI | LOLPE | GALAP | LAMPU | MATIN | PAPRH | STEME | VERPE | VIOAR |
|---|---|---|---|---|---|---|---|---|---|---|---|---|---|
| CTP | 0.240 | 100 | 100 | 100 | 100 | 100 | 95 | 100 | 100 | 100 | 100 | 100 | 100 |
| | 0.120 | 99 | 100 | 100 | 100 | 98 | 93 | 100 | 99 | 100 | 100 | 100 | 100 |
| | 0.060 | 35 | 100 | 100 | 100 | 95 | 65 | 100 | 99 | 100 | 100 | 100 | 100 |
| | 0.030 | 15 | 100 | 100 | 98 | 93 | 10 | 90 | 98 | 100 | 80 | 100 | 99 |
| REF-4 | 0.240 | 98 | 100 | 100 | 100 | 100 | 90 | 100 | 100 | 100 | 100 | 100 | 100 |
| | 0.120 | 93 | 100 | 100 | 100 | 100 | — | 100 | 100 | 100 | 100 | 100 | 100 |
| | 0.060 | 92 | 100 | 100 | 80 | 98 | — | 100 | 100 | 100 | 100 | 100 | 100 |
| | 0.030 | 20 | 100 | 100 | 65 | 98 | — | 97 | 100 | 100 | 92 | 98 | 99 |
| REF-5 | 0.240 | 35 | 100 | 100 | 100 | 99 | — | 100 | 100 | 100 | 70 | 100 | 99 |
| | 0.120 | 30 | 100 | 100 | 95 | 98 | 50 | 55 | 100 | 100 | 35 | 95 | 98 |
| | 0.060 | 15 | 100 | 100 | 50 | 90 | 5 | 20 | 100 | 95 | 25 | 93 | 97 |
| | 0.030 | 5 | 100 | 92 | 20 | 40 | 2 | 0 | 85 | 85 | 10 | 55 | 96 |
| REF-6 | 0.240 | 99 | 100 | 100 | 100 | 100 | 97 | 100 | 100 | 100 | 100 | 100 | 99 |
| | 0.120 | 97 | 100 | 100 | 100 | 100 | 65 | 100 | 100 | 100 | 100 | 100 | 99 |
| | 0.060 | 60 | 100 | 100 | 100 | 100 | — | 100 | 100 | 100 | 100 | 100 | 99 |
| | 0.030 | 30 | 100 | 100 | 100 | 95 | — | 85 | 99 | 100 | 97 | 96 | 99 |
| REF-7 | 0.240 | 90 | 100 | 100 | 100 | 99 | 92 | 100 | 100 | 100 | 100 | 100 | 99 |
| | 0.120 | 65 | 100 | 100 | 93 | 97 | 65 | 93 | 100 | 100 | 98 | 99 | 99 |
| | 0.060 | 35 | 100 | 95 | 85 | 90 | — | 90 | 100 | 100 | 98 | 90 | 99 |
| | 0.030 | 10 | 100 | 95 | 35 | 75 | — | 30 | 90 | 95 | 25 | 70 | 98 |
| REF-8 | 0.240 | 90 | 100 | 100 | 100 | 99 | 70 | 100 | 100 | 100 | 100 | 100 | 100 |
| | 0.120 | 70 | 100 | 100 | 90 | 99 | 70 | 100 | 100 | 100 | 100 | 100 | 100 |
| | 0.060 | 35 | 100 | 100 | 90 | 97 | — | 100 | 100 | 100 | 85 | 100 | 99 |
| | 0.030 | 15 | 100 | 100 | 60 | 60 | 3 | 98 | 95 | 100 | 35 | 100 | 99 |

TABLE 4

| | | Pre-emergence application 3 weeks after treatment (Selectivity) | |
|---|---|---|---|
| Treatment | Dose kg/ha | TRZAWK | TRZAWM |
| CTP | 0.240 | 5 | 5 |
| | 0.120 | 1 | 2 |
| | 0.060 | 0 | 1 |
| | 0.030 | 0 | 0 |
| REF-4 | 0.240 | 22 | 35 |
| | 0.120 | 22 | 22 |
| | 0.060 | 15 | 8 |
| | 0.030 | 10 | 15 |
| REF-5 | 0.240 | 8 | 8 |
| | 0.120 | 1 | 1 |
| | 0.060 | 0 | 0 |
| | 0.030 | 0 | 0 |
| REF-6 | 0.240 | 25 | 25 |
| | 0.120 | 12 | 15 |
| | 0.060 | 10 | 8 |
| | 0.030 | 0 | 1 |
| REF-7 | 0.240 | 18 | 10 |
| | 0.120 | 5 | 5 |
| | 0.060 | 5 | 5 |
| | 0.030 | 2 | 2 |
| REF-8 | 0.240 | 18 | 18 |
| | 0.120 | 12 | 15 |
| | 0.060 | 5 | 3 |
| | 0.030 | 1 | 1 |

Wheat

CTP was sufficiently selective in wheat at the highest dose of 240 g/ha. However, complete control of all the grasses such as Alopecurus and Setaria and broadleaf weeds such as Galium was already achieved at 120 g/ha, demonstrating the excellent safety margin of this compound for wheat selective weed control.

Only one tested prior art compound, REF-5, was similarly selective in wheat as CTP at the highest dose of 240 g/ha; however, it was clearly less active on key weed species such as Alopecurus, Setaria, Lolium or Galium.

The remaining compounds of the prior art were considerably less tolerant in wheat than the compound of the invention. The maximum tolerated dose in wheat was 240 g/ha for REF-7, 120 g/ha for REF-6 and REF-8, and 60 g/ha for REF-4. At these doses the compounds of the prior art did not match the performance of CTP, being inferior in activity on either Alopecurus, Setaria or Galium; hence, none of these compounds provided complete weed control at wheat selective doses, and comparable selectivity in wheat compared to the compound of the invention.

Conclusions

CTP was sufficiently selective in wheat at 240 g/ha, while complete pre-emergence control of all the grasses and broadleaf weeds including Alopecurus, Galium and Lolium was observed at 120 g/ha, thus proving the excellent safety margin of this compound for wheat selective cross spectrum control of both grasses and broadleaf weeds. In contrast, none of the tested prior art compounds provided complete weed control at wheat selective doses. In addition, the most active compounds of the prior art were clearly less selective in wheat than CTP. Accordingly the compound of the invention shows promising potential for pre-emergence weed control in wheat.

2. Post-Emergence Test

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels equivalent of about 0.030 to 0.240 kg per hectare of test compound per pot. After spraying the plants are placed an greenhouse benches and are cared for in the usual manner, commensurate with conventional greenhouse practices. From 2 to 4 weeks after treatment, the seedling plants are examined and rated according to the rating system provided above. A rating 0 indicates growth as untreated control, a rating 100 indicates death. The results of the test are set out in Tables 5 and 6 below.

TABLE 5

| Treatment | Dose kg/ha | Post-emergence application 2–4 weeks after treatment (Weed control) SETVI | GALAP | LAMPU | MATIN | POLCO | STEME | VIOAR |
|---|---|---|---|---|---|---|---|---|
| TTP | 0.240 | 100 | 93 | 93 | 90 | 90 | 90 | 95 |
| | 0.120 | 97 | 80 | 92 | 75 | 35 | 70 | 92 |
| | 0.060 | 97 | 97 | 75 | 90 | 60 | 60 | 92 |
| | 0.030 | 93 | 60 | 85 | 50 | 10 | 50 | 90 |
| REF-1 | 0.240 | 100 | 92 | 93 | 85 | 70 | 92 | 95 |
| | 0.120 | 100 | 92 | 93 | 75 | 25 | 92 | 93 |
| | 0.060 | 99 | 85 | 93 | 75 | — | 90 | 93 |
| | 0.030 | 99 | 80 | 93 | 70 | 15 | 80 | 92 |
| REF-2 | 0.240 | 100 | 85 | 93 | 60 | 40 | 80 | 95 |
| | 0.120 | 96 | 85 | 92 | 55 | 25 | 55 | 90 |
| | 0.060 | 55 | 80 | 90 | 45 | 0 | 50 | 90 |
| | 0.030 | 30 | 50 | 85 | 35 | — | 45 | 75 |
| REF-3 | 0.240 | 100 | 93 | 93 | 85 | 80 | 92 | 93 |
| | 0.120 | 99 | 93 | 93 | 85 | 55 | 85 | 90 |
| | 0.060 | 98 | 90 | 93 | 80 | 35 | 85 | 90 |
| | 0.030 | 95 | 90 | 93 | 65 | — | 65 | 90 |

TABLE 6

| Treatment | Dose kg/ha | Post-emergence application 2–4 weeks after treatment (Selectivity) TRZAWK | TRZAWM |
|---|---|---|---|
| TTP | 0.24 | 15 | 12 |
| | 0.12 | 8 | 8 |
| | 0.06 | 8 | 8 |
| | 0.03 | 2 | 1 |
| REF-1 | 0.24 | 40 | 45 |
| | 0.12 | 30 | 30 |
| | 0.06 | 25 | 22 |
| | 0.03 | 18 | 15 |
| REF-2 | 0.24 | 10 | 8 |
| | 0.12 | 8 | 8 |
| | 0.06 | 5 | 5 |
| | 0.03 | 3 | 2 |
| REF-3 | 0.24 | 35 | 30 |
| | 0.12 | 25 | 22 |
| | 0.06 | 15 | 15 |
| | 0.03 | 12 | 10 |

Wheat

TTP was sufficiently selective in wheat at the highest dose of 240 g/ha. At this dose all of the species included in test were well controlled, including Setaria viridis, an important grass species particularly in Canadian cereals, and Galium and Matricaria, both of which are important key broadleaf weed species in European cereals.

Only one tested prior art compound, REF-2, was similarly selective in wheat. However, this compound showed less overall activity than TTP.

REF-1 and REF-3 were clearly less selective in wheat than TTP. The maximum tolerated dose in barley for REF-3 was 60 g/ha. REF-1 was not tolerated in wheat at any dose. Contrary to the findings with TTP the weed spectrum controlled by REF-3, was incomplete at wheat selective rates.

CONCLUSIONS

TTP was the only compound that provided complete postemergence control of all the grasses and broadleaf weeds including Setaria, Galium, Matricaria, Polygonum, Stellaria and Viola at wheat selective doses.

Taking into account the outstanding activity of TTP both in preemergence and post-emergence application, this compound was clearly superior to the compounds of the prior art with regard to cereal selective control of important grasses and broadleaf weeds.

The invention claimed is:

1. A compound of formula I

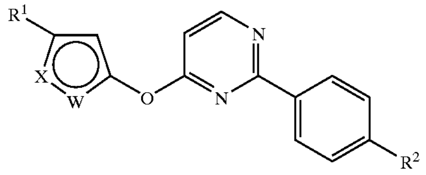

(I)

in which

X—W represents N—N($CH_3$), N—CH—CH or CH—CH—CH;

$R^1$ represents a halogen atom or a haloalkyl or haloalkoxy group and $R^2$ represents a halogen atom or a haloalkyl group.

2. A compound of formula I according to claim 1 wherein

X—W represents N—CH—CH or CH—CH—CH;

X—W represents N—CH—CH or CH—CH—CH;

$R^1$ represents a halogen atom; and $R^2$ represents a $C_{1-4}$ fluoroalkyl group.

3. 4-(3-Trifluoromethylphenoxy)-2-(trifluoromethyl-phenyl)-pyrimidine or 4-(2-chloropyrid-4-yloxy)-2-(4-trifluoromethyl-phenyl)-pyrimidine.

4. A composition comprising a herbicidally active amount of at least one compound of formula I as claimed in any of claims 1 to 3, and at least one carrier.

5. A method of combating growth of undesired plants in cereals, which comprises treating a locus with an effective amount of a compound of formula I:

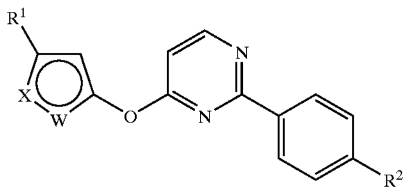

(I)

in which

X—W represents N—N($CH_3$), N—CH—CH or CH—CH—CH;

$R^1$ represents a halogen atom or a haloalkyl or haloalkoxy group; and $R^2$ represents a halogen atom or a haloalkyl group.

6. A method according to claim 1 wherein

X—W represents N—CH—CH or CH—CH—CH;

$R^1$ represents a halogen atom or a $C_{1-4}$ fluoroalkyl group; and $R^2$ represents a $C_{1-4}$ fluoroalkyl group.

7. A method according to claim 1 wherein said compound is 4-(3-trifluoromethylphenoxy)-2-(4-trifluoromethyl-phenyl)-pyrimidine or 4-(2-chloropyrid-4-yloxy)-2-(4-trifluoromethyl-phenyl)-pyrimidine.

8. A method according to claim 1 wherein the undesired plants are grasses selected from Alopecurus, Apera and Poa.

9. A method according to claim 8 wherein the compound is applied to the locus before the undesired plants emerge from the soil.

10. A method according to claim 8 wherein the undesired plants are selected from Alopecurus myosuroides, Apera spica-venti and Poa annua.

11. A method of combating Apera according to claim 8 wherein the application rate of said compound to the locus is approximately from 0.03 to 0.15 kg/ha.

12. A method according to claim 1 wherein the undesired plants are broadleaf weeds selected from Galium, Matricaria and Stellaria.

13. A method according to claim 12 wherein the compound is applied to the locus after the undesired plants have emerged from the soil.

14. A method according to claim 12 wherein the undesired plants are selected from Galium aparinae, Matricaria inodora and Stellaria media.

15. A method according to claim 12 wherein the application rate of said compound to the locus is approximately from 0.05 to 0.15 kg/ha.

16. A method of combating grasses selected from Alopecurus and Poa according to claim 1 in which the application rate of said compound to the locus is approximately from 0.15 to 0.28 kg/ha.

17. A method according to claim 1 wherein the application rate of said compound to the locus is approximately from 0.02 to 0.30 kg/ha.

18. A method according to claim 17 wherein said application comprises spraying the locus with a liquid formulation containing said a compound.

19. A method according to claim 18 wherein the formulation is sprayed onto soil at the locus.

20. A method according to claim 18 wherein the formulation is sprayed onto plant leaves at the locus.

21. A method according to claim 17 wherein

X—W represents N—CH—CH or CH—CH—CH;

$R^1$ represents a halogen atom or a $C_{1-4}$ fluoroalkyl group; and $R^2$ represents a $C_{1-4}$ fluoroalkyl group.

22. A method according to claim 21 wherein the cereal is winter wheat, winter barley, or both.

23. A method according to claim 1 wherein the cereal is winter wheat, winter barley, or both.

* * * * *

UNITED STATES PATENT AND TRADEMARK OFFICE

CERTIFICATE OF CORRECTION

PATENT NO. : 7,008,905 B2 Page 1 of 1
APPLICATION NO. : 09/861006
DATED : March 7, 2006
INVENTOR(S) : Baltruschat et al.

It is certified that error appears in the above-identified patent and that said Letters Patent is hereby corrected as shown below:

In Claim 1, column 16, line 48 please delete:
"$R^1$ represents a halogen atom or a haloalkyl or haloalkoxy" and substitute therefore:
-- $R^1$ represents a halogen atom or a haloalkoxy --

In Claim 3, column 16, lines 58-60 please delete:
"4-(3-Triflouromethylphenoxy)-2-(triflouromethyl-phenyl)-pyrimidine or 4-(2-chloropyrid-4-yloxy)-2-(4-triflouromethyl-phenyl)-pyrimidine" and substitute therefore:
-- 4-(2-Cholorpyrid-4-yloxy)-2-(4-triflouromethyl-phenyl)-pyrimidine --

Signed and Sealed this

First Day of August, 2006

JON W. DUDAS
*Director of the United States Patent and Trademark Office*